US007074566B2

(12) United States Patent
Wolf et al.

(10) Patent No.: US 7,074,566 B2
(45) Date of Patent: Jul. 11, 2006

(54) METHOD FOR TESTING HORMONAL EFFECTS OF SUBSTANCES

(75) Inventors: Siegmund Wolf, Bad Klosterlausnitz (DE); Maik Obendorf, Weimar (DE); Rene Meyer, Reichenbach (DE); Jens Schroeder, Jena (DE)

(73) Assignee: Schering AG, Berlin (DE)

( * ) Notice: Subject to any disclaimer, the term of this patent is extended or adjusted under 35 U.S.C. 154(b) by 229 days.

(21) Appl. No.: 10/456,269

(22) Filed: Jun. 6, 2003

(65) Prior Publication Data

US 2003/0232376 A1    Dec. 18, 2003

(30) Foreign Application Priority Data

Jun. 12, 2002    (DE) ............................... 102 26 675

(51) Int. Cl.
   *C12Q 1/68*      (2006.01)
   *G01N 33/53*   (2006.01)

(52) U.S. Cl. ......................................... 435/6; 435/7.1
(58) Field of Classification Search .................... 435/6, 435/320.1
   See application file for complete search history.

(56) References Cited

OTHER PUBLICATIONS

Cote et al Sam68 RNA bindig protein is an in vivo substrate for protein arginine N-methyltransferase 1 Molecular Biology of the Cell vol. 14 pp. 274-287 2003.*
Chao Qi et al.: "Identification of Protein Arginine Methyltransferase . . . ", The Journal of Biological Chemistry, vol. 277, No. 32, Issue of Aug. 9, pp. 28624-28630, 2002.
Hamisch S. Scott et al: "Identification and Characterization of . . . ", Genomics 48, 330-340, 1998, pp. 330-340.
M Beato et al: "Steroid Hormone Receptors: An Update" In Human Reproduction Update 2000, vol. 6, No. 3, pp. 225-236.
David J. Mangelsdorf et al: "The RXR Heterodimers and . . . ", Cell, Col. 83, pp. 841-850, Dec. 1995.
Neil J. McKenna et al: "Nuclear Recptor Coregulators . . . " Endocrine Reviewsvol. 20, No. 3 : pp. 321-344, 1999.
A.O. Brinkmann et al: "Mechanism of Adrogen Receptor Activation . . . ", Journal of Steroid Biochemistry and Molecular Biology 69, 1999, pp. 307-313.

Xiu Fen Ding, et al: "Nuclear Receptor-Binding Sites . . . ", Molecular Endocrinology, 1998, vol. 12, No. 2, pp. 302-313.
Daniel Robyr et al: "Nuclear Hormone Receptor . . . ", Molecular Endocrinology, 2000, vol. 14, No. 3, pp. 329-347.
Jian Li and Peter Vogt: "The Retroviral Oncogene . . . "Proc. Natl. Acad. Sci. USA, vol. 90, pp. 4490-4494, May 1993.
Hamisg S. Scott, et al: "Identification and Characterization of Two Putative . . . " vol. 48, Issue 3, Mar. 15, 1998, Abstract.
Julia Kzhyshkowska, et al: "Heterogeneous Nuclear Ribonucleoprotein . . . " Biochem J. (2001) 358, pp. 305-314.
Chao Qi et al: "Identification of Protein Arginine . . . " The Journal of Biological Chemistry, vol. 277, No. 32, Issue of Aug. 9, pp. 28624-28630, 2002.
Eric R. Schuur, et al: "Ligand-Dependent Interaction of Estrogen . . . " The Journal of Biological Chemistry, vol. 276, No. 36, Issue of Sep. 7, pp. 33554-22560, 2001.
Chao Qi et al: "Identification of PRMT2 as a Coativator . . . "J. Biol Chem, 10.1074.JBC.M201053200, Abstract., Aug. 2002.
Blast 2 Sequences Results, HTTP://WWW.NCBI.NLM.NIH.GOV., Aug. 26, 2002.
X00209.H.Sapiens . . . , NCBI Sequence Viewer, HTTP://WWW.NCBI.NLM.NIH.GOV., Feb. 28, 2003.
NM_001535.Homo Sapiens . . . , NCBI Sequence Viewer, HTTP://WWW.NCBI.NLM.NIH.GOV., Feb. 28, 2003.

* cited by examiner

*Primary Examiner*—James Ketter
*Assistant Examiner*—Konstantina Katcheves
(74) *Attorney, Agent, or Firm*—Michael J. Striker

(57) ABSTRACT

The method for testing of substances for hormonal effects, especially for androgenic or anti-androgenic effects, includes exposing cells transfected with two vectors to the substances, wherein one vector contains a DNA, which codes for a nuclear receptor protein, or a fragment thereof, especially a human nuclear receptor protein, or a fragment thereof, and the other vector contains a DNA, which codes for the HSRNAAM co-modulator, or a fragment thereof; and measuring transcription activity, which the nuclear receptor protein, or its fragment, activates or releases in the presence of the HSRNAAM co-modulator, or its fragment, and/or measuring the influence of the substance on the interaction between the nuclear receptor protein, or its fragment, and the HSRNAAM co-modulator, or its fragment, by protein-protein interaction or by protein-protein-DNA interaction. Also a method for determining interference in the co-modulation mechanism between androgen receptor protein and HSRNAAM co-modulator is described.

9 Claims, 4 Drawing Sheets

SEQUENCE LISTING

```
<160> NUMBER OF SEQ ID NOS: 3

<210> SEQ ID NO 1
<211> LENGTH: 1779
<212> TYPE: DNA
<213> ORGANISM: Homo sapiens
<220> FEATURE:
<221> NAME/KEY: Entire DNA sequence codes for human androgen receptor
      protein
<222> LOCATION:
<223> OTHER INFORMATION:

<400> SEQUENCE: 1
gcagggagct ccgggacact tgaactgccg tctaccctgt ctctctacaa gtccggagca      60
ctggacgagg cagctgcgta ccagagtcgc gactactaca actttccact ggctctggcc    120
ggaccgccgc cccctccgcc gcctccccat ccccacgctc gcatcaagct ggagaacccg    180
ctggactacg gcagcgcctg ggcggctgcg gcggcgcagt gccgctatgg ggacctggcg    240
agcctgcatg gcgcgggtgc agcgggaccc ggttctgggt caccctcagc cgccgcttcc    300
tcatcctggc acactctctt cacagccgaa gaaggccagt tgtatggacc gtgtggtggt    360
ggtgggggtg gtggtggcgg cggcggcggc ggcggcggcg gcggcggcgg cggcggcggc    420
ggcggcggcg gcggcgaggc ggaagctgta gcccccacg gctacactcg gcccctcag    480 gggctggcgg gccaggaaag cgacttcacc gcacctgatg tgtggtaccc tggcggcatg    540
gtgagcagag tgccctatcc cagtcccact tgtgtcaaaa gcgaaatggg ccctggatg    600 gatagctact ccggacctta cggggacatg cgtttggaga ctgccaggga ccatgttttg    660
cccattgact attactttcc accccagaag acctgcctga tctgtggaga tgaagcttct    720
gggtgtcact atggagctct cacatgtgga agctgcaagg tcttcttcaa aagagccgct    780
gaagggaaac agaagtacct gtgcgccagc agaaatgatt gcactattga taaattccga    840
aggaaaaatt gtccatcttg tcgtcttcgg aaatgttatg aagcagggat gactctggga    900
gcccggaagc tgaagaaact tggtaatctg aaactacagg aggaaggaga ggcttccagc    960
accaccagcc ccactgagga gacaacccag aagctgacag tgtcacacat tgaaggctat   1020
gaatgtcagc ccatctttct gaatgtcctg gaagccattg agccaggtgt agtgtgtgct   1080
ggacacgaca acaaccagcc cgactccttt gcagccttgc tctctagcct caatgaactg   1140
ggagagagac agcttgtaca cgtggtcaag tgggccaagg ccttgcctgg cttccgcaac   1200
ttacacgtgg acgaccagat ggctgtcatt cagtactcct ggatggggct catggtgttt   1260
```

-continued

```
gccatgggct ggcgatcctt caccaatgtc aactccagga tgctctactt cgccctgat      1320 ctggttttca atgagtaccg catgcacaag tcccggatgt acagccagtg tgtccgaatg      1380
aggcacctct ctcaagagtt tggatggctc caaatcaccc cccaggaatt cctgtgcatg      1440
aaagcactgc tactcttcag cattattcca gtggatgggc tgaaaaatca aaaattcttt      1500
gatgaacttc gaatgaacta catcaaggaa ctcgatcgta tcattgcatg caaaagaaaa      1560
aatcccacat cctgctcaag acgcttctac cagctcacca agctcctgga ctccgtgcag      1620
cctattgcga gagagctgca tcagttcact tttgacctgc taatcaagtc acacatggtg      1680
agcgtggact ttccggaaat gatggcagag atcatctctg tgcaagtgcc caagatcctt      1740
tctgggaaag tcaagcccat ctatttccac acccagtga                             1779
```

<210> SEQ ID NO 2
<211> LENGTH: 1302
<212> TYPE: DNA
<213> ORGANISM: Artificial Sequence
<220> FEATURE:
<221> NAME/KEY: Codes for amino acids 1 to 433 of HSRNAAM co-modulator protein
<222> LOCATION:
<223> OTHER INFORMATION: Deposited under DSM 15041 in German Collection for Microorganisms and Cell Cultures

<400> SEQUENCE: 2

```
atggcaacat caggtgactg tcccagaagt gaatcgcagg gagaagagcc tgctgagtgc      60
agtgaggcgg gtctcctgca ggagggagta cagccagagg agtttgtggc catcgcggac     120
tacgctgcca ccgatgagac ccagctcagt tttttgagag agaaaaaat tcttatcctg     180 agacaaacca ctgcagattg gtggtggggt gagcgtgcgg gctgctgtgg gtacattccg     240
gcaaaccatg tggggaagca cgtggatgag tacgaccccg aggacacgtg gcaggatgaa     300
gagtacttcg gcagctatgg aactctgaaa ctccacttgg agatgttggc agaccagcca     360
cgaacaacta ataccacag tgtcatcctg cagaataaag aatccctgac ggataaagtc     420
atcctggacg tgggctgtgg gactgggatc atcagtctct ctgtgcacac ctatgcgcgg     480
cctagagcgg tgtacgcggt ggaggccagt gagatggcac agcacacggg gcagctggtc     540
ctgcagaacg gctttgctga catcatcacc gtgtaccagc agaaggtgga ggatgtggtg     600
ctgcccgaga aggtggacgt gctggtgtct gagtggatgg ggacctgcct gctgtttgag     660
ttcatgatcg agtccatcct gtatgcccgg gatgcctggc tgaaagagga cggggtcatt     720
tggcccacca tggctgcgtt gcaccttgtg ccctgcagtg ctgataagga ttatcgtagc     780
aaggtgctct ctctgggacaa cgcgtacgag ttcaacctca cgctctgaa atctttagca     840 gttaaggagt ttttttcaaa gcccaagtat aaccacattt gaaaccaga agactgtctc     900 tctgaaccgt gcactatatt gcagttggac atgagaaccg tgcaaattc tgatctagag     960 accctgaggg gcgagctgcg cttcgacatc aggaaggcgg ggaccctgca cggcttcacg    1020
gcctggttta gcgtccactt ccagagcctg caggaggggc agccgccgca ggtgctcagc    1080 accgggcct tccaccccac cacacactgg aagcagacgc tgttcatgat ggacgaccca    1140
gtccctgtcc atacaggaga cgtggtcacg ggttcagttg tgttgcagag aaacccagtg    1200
tggagaaggc acatgtctgt ggctctgagc tgggctgtca cttccagaca agaccccaca    1260
tctcaaaaag ttggagaaaa agtcttcccc atctggagat ga                      1302
```

<210> SEQ ID NO 3

-continued

```
<211> LENGTH: 492
<212> TYPE: DNA
<213> ORGANISM: Artificial Sequence
<220> FEATURE:
<221> NAME/KEY: Codes for amino acids 271 to 433 of HSRNAAM protein
      fragment
<222> LOCATION:
<223> OTHER INFORMATION: Deposited under DSM 15042 in German Collection
      for Microorganisms and Cell Cultures

<400> SEQUENCE: 3
ttcaacctca gcgctctgaa atctttagca gttaaggagt tttttcaaa gcccaagtat      60 aaccacattt tgaaaccaga agactgtctc tctgaaccgt gcactatatt gcagttggac    120
atgagaaccg tgcaaatttc tgatctagag accctgaggg gcgagctgcg cttcgacatc    180
aggaaggcgg ggaccctgca cggcttcacg gcctggttta gcgtccactt ccagagcctg    240
caggaggggc agccgccgca ggtgctcagc accgggccct tccacccac cacacactgg     300 aagcagacgc tgttcatgat ggacgaccca gtccctgtcc atacaggaga cgtggtcacg    360
ggttcagttg tgttgcagag aaacccagtg tggagaaggc acatgtctgt ggctctgagc    420
tgggctgtca cttccagaca agacccaca tctcaaaaag ttggagaaaa agtcttcccc     480
atctggagat ga                                                        492
```

US 7,074,566 B2

METHOD FOR TESTING HORMONAL EFFECTS OF SUBSTANCES

BACKGROUND OF THE INVENTION

The present invention relates to a method of testing the hormonal effect of substances, and, particularly, to a method of determining interference or disturbance in the co-modulation mechanism between androgen receptor proteins and the coactivator arginine methyltransferase (HSRNAAM).

During evaluation of substances for possible pharmaceutical use it is generally common to test these substances for contingent hormonal action, especially for possible androgenic or anti-androgenic activity. Knowledge of the hormonal effects, especially of androgenic or anti-androgenic effects, of these substances is important in many cases in administration of pharmacologically active substances, since they can bring about undesirable side effects in patients. To test the hormonal action of the various substances, the ability of the substances to bind to hormonal receptors and activate their transcription activity is especially measured.

Knowledge of the hormonal effects of substances is of interest not only for potential pharmaceutical, but also for non-pharmaceutical, substances, since it is assumed that many substances present in the surroundings can have androgenic or anti-androgenic and/or estrogenic or anti-estrogenic activity. It is possible that some of these substances produce undesirable deleterious effects.

There is also a considerable need for a method and for a suitable means for performing the method, with which an answer regarding the hormonal effects of substances can be obtained in a reliable, sensitive, simple, economical and rapid manner. The currently known methods are not sufficient.

SUMMARY OF THE INVENTION

It is therefore an object of the present invention to provide a method and a suitable means for obtaining information regarding hormonal effects of substances to be tested in a reliable, sensitive, simple, economical and rapid manner.

According to the invention this object is attained in a surprising manner by a method for testing of a substance for hormonal effects, especially for androgenic or anti-androgenic effects, comprising the steps of:

a) exposing cells transfected with two vectors to the substance, wherein one vector contains a DNA, which codes for a nuclear receptor protein or a fragment thereof, especially a human nuclear receptor protein or a fragment thereof, and the other vector contains a DNA, which codes for the HSRNAAM comodulator or a fragment thereof; and b) measuring transcription activity, which the nuclear receptor protein, or its fragment, activates or releases in the presence of the HSRNAAM comodulator, or its fragment, and/or the influence of the substance on the interaction between the nuclear receptor protein, or its fragment, and HSRNAAM comodulator, or its fragment, by protein-protein interaction or protein-protein-DNA interaction.

It was surprisingly found that whether or not substances, which, for example, can be environmentally relevant or of pharmacological interest, have a hormonal effect, especially an androgenic or anti-androgenic effect, can be determined with the method according to the invention in a reliable, sensitive, rapid, simple and economical manner.

In the method according to the invention cells transformed with a vector are used. The vector has DNA, which codes for a nuclear receptor protein or a fragment thereof.

The super-family of the nuclear receptors (NRs), to which more than 50 different proteins belong, is a group of related transcription factors, which control the transcription of respective target genes like reactions at specific ligands, e.g. hormones. The families can be divided into subfamilies according to certain characteristics, such as e.g. dimerization status, the type of ligands or the structure of the DNA reaction elements (Beato, et al, Human Reproduction. Update, 6, pp. 225 to 236 (2000)). The conforming or corresponding structure of the functional domain (designated A to F) is a characteristic feature of the NRs. It has a strongly variable, only weakly preservative, N-terminal region with autonomic constitutive activating function (AF-1) a strongly conservative DNA binding domain (DBD), which is responsible for detection of special DNA reaction elements and comprises two zinc finger motifs. It has a variable hinged domain and conservative multifunctional C-terminal ligand-binding domain (LDB) with dimerization and ligand-dependent transactivation function (AF-2). Following that there is a region at the furthest terminal carbon, whose function is not known and absent in some receptors, such as PR (progesterone receptor), PPAR (peroxisome proliferator-activated receptor) and RXR (retinoid-X-receptor) (Mangelsdorf & Evans, Cell, 83, pp. 841–850 (1995); Robyr, et al, Mol. Endocrinol., 14, pp. 329 to 347 (2000)). For a few NRs (e.g. Androgen-receptors (AR)) it is known that the N-terminal region is in a position to interact with the C-terminal region (Brinkmann, et al, J. Steroid Biochem. And Mol. Biol., 69, pp. 307–313 (1999)). Steroid hormone receptors, such as e.g. estrogen (ER), progesterone (PR), glucocorticoid (GR), mineral corticoid (MR) and androgen receptors (AR) bind steroidal ligands, which are derived from pregnenolone, such as progestin, the estrogens, the glucocorticoids and the mineral corticoids, as well as the androgens, bind steroid ligands. The ligand binding activates the receptors and controls expression of the suitable target genes.

As previously explained in step a) of the method according to the invention cells are used which contain a vector which contains DNA coding for the co-modulator HSRNAAM or a fragment thereof.

The so-called co-modulators are classes of proteins, which act as bridging molecules between the transcription initiation complex and the NRs in activation (co-activation) and/or repression (co-repression) of gene transcription (McKenna, et al, Endocr. Rev., 20, pp. 321 to 347 (1999)). A co-activator must be able to amplify or magnify the receptor function and to directly integrate with the activated domains of NRs in the presence of an agonist. It must also interact with the basal transcription apparatus and finally it may not amplify the basal transcription activation by itself. Most co-modulators interact with the help of one or more LXXLL-motif(s) (NR boxes) with the AF-2 domain of NRs. However some co-modulators were described which interact with other NR regions (Ding, et al, Mol. Endocrinol., 12, pp. 302 to 313 (1998)). Chao Qui, et al, describe the protein PRMT2 (protein arginine methyltransferase 2) as co-activator for ERα (JBC Papers in Press, Manuscript M201053200, May 30, 2002).

In the method according to the invention the co-modulator designated with arginine methyl transferase (HSRNAAM) or especially the fragment of HSRNAAM comprising amino acids 271 to 433 is used. The c-DNA sequence has been described (Genbank X99209) and code for 433 amino acids (Scott, et al, Genomics, 48, pp. 330 to 349 (1998)). The DH5 alpha E. coli clones, which contain plasmids coding for the amino acids 1 to 433 and/or 271 to 433 of HSRNAAM, were deposited in the German Collection for Microorganisms and Cell Cultures on Jun. 5, 2002 under DSM 15041 and DSM 15402.

The method according to the invention can be performed using these proteins in an especially reliable, sensitive, simple, economical and rapid manner. Furthermore the HSRNAAM fragments, especially the fragments having amino acids 271 to 433 of HSRNAAM, have the advantage that they are easily manipulated and cloned, however they still have the functional properties of HSRNAAM.

HSRNAAM is a co-activator for human androgen receptors and other nuclear receptors, which amplifies the interaction between an androgen and the receptor. The sequence of HSRNAAM is already described in Genbank X99209; generally no interaction with nuclear receptors, especially the androgen receptor, is described there. The invention is based on the surprising knowledge or understanding that nuclear receptors, especially the AR, on the one hand, and HSRNAAM, on the other hand, interact and the AR-mediated transactivation is magnified or augmented. HSRNAAM is a protein, which functions as co-mediator, since it amplifies or represses the transcription effect after binding of steroids to the nuclear receptors and promotes binding and activation of nuclear receptors to molecules, to which no hormonal activation was attributed formerly.

HSRNAAM represents a co-activator for the androgen receptor and other nuclear receptors, such as estrogen receptor α, estrogen receptor β, progesterone receptor A, progesterone receptor B, glucocorticoid receptor, mineral corticoid receptor, thyroid gland hormone receptor, Vitamin-D receptor, peroxisome proliferator-activater receptor, retinic acid receptor, retinoid X receptor and orphan receptors. These receptors are preferred for use in the present invention, since the advantages of the method according to the invention are obtained in an especially good manner with them.

Vectors, which code for fragments of the preceding or above-mentioned proteins, can also be used in the method according to the invention. The expression "fragments" should be understood in connection with aforementioned proteins, which have an amino acid or several amino acids less than the full length proteins and still have the functioning properties of a nuclear receptor or a co-modulator.

As already described above, in step a) of the method according to the present invention cells that are transfected with two vectors, which contain DNA coding for special proteins, are used. These cells are thus in a position to express both different proteins.

Preferably the cells are from established cell lines and/or eukaryotic cells, especially prostate cells, nerve cells, glia cells, fibroblasts, blood cells, osteoblasts, osteoclasts, hepatocytes, epithelial cells or muscle cells. The method according to the invention can be performed rapidly and economically with the established cell lines. Especially advantageous results can be obtained using the eukaryotic cells, especially the above-described eukaryotic cells.

In a preferred embodiment of the method according to the invention eukaryotic expression vectors are used, e.g. pCMX, pCMV or pSG5. The method according to the invention can be performed in an especially advantageous and rapid manner and especially outstanding results can be obtained using these vectors, especially in combination with the above-mentioned stable cell lines and/or eukaryotic cells.

Methods for insertion of the DNA coding the preceding proteins in vectors, for introducing the vectors into cells and for culturing the cells so obtained under suitable culture conditions so that these proteins can be expressed, and materials required for those purposes, are known to those skilled in the art.

According to step b) of the method according to the invention the transcription activity is measured, which the nuclear receptor protein or its fragment produces in the presence of the co-modulator or its fragment. This can occur, for example, by detection of a reporter gene.

Reporter genes are genes or gene fragments, which are coupled with other genes or regulator sequences, in order to make the activity of these sequences detectable. Reporter genes produce gene products, which are as easily detectable as possible, for example photometrically by color reaction. Frequently used reporter genes are the genes for β-galactosidase, the gene for alkaline phosphatase, the gene for chloramphenicol-acetyl transferase, the gene for catechol dioxygenase, the gene for the "green fluorescent protein" and different Luciferase genes, which induce the cells to product light.

These reporter genes can likewise be introduced into the cells with vectors, especially eukaryotic expression vectors. For example a vector, which contains DNA coding for a reporter gene, is the MMTV Luciferase vector, which is used for measuring the androgenic activity of substances.

Substances with a hormonal effect, especially with an androgenic/antiandrogenic effect, are then detectable by an elevated or reduced activity of the reporter gene.

The measurement of the influence of the test substance on the interaction between the receptor or its fragment and the co-modulator or its fragment can also occur by determination of the protein-protein interaction. For example, this can take place by twin hybrid systems, immune precipitation, GST pull-down assays, FRET analysis and ABCD assays and determination of protein-protein DNA interaction, for example by gel retardation assays.

It has been found further that HSRNAAM can be used as a very good indicator of androgenic-conditioned maladies or illnesses. Relevant androgenic-conditioning illnesses or maladies, such as prostate cancer, erectile dysfunction, infertility, grain or glaze formation, acne or hypogonadism and androgen resistant syndromes, such as testicular feminization, are based on defects in or interference with the co-modulation mechanism between AR and HSRNAAM. In patients with these types of illnesses the possibility exists for measurement of relative concentrations of AR and HSR-NAAM outside the body. This is possible by use of quantitative methods for measuring relative amounts of both molecules in respective patients, in which for example antibodies can be used both against AR and also against HSRNAAM or nucleic acid probes can be used against their mRNA. There are several methods for measuring these comparative processes, which are known to one skilled in the art. One skilled in the art also knows suitable materials and apparatus for use in these methods. These methods include radioimmunoassay, ELISA tests, immunodyes, RT-PCR, Western Blot or Northern Blot, DNA chip or protein chip. Furthermore it is possible to construct probes for a PCR assay in the usual manner with the help of the HSR-NAAM-cDNA. Mutations of the normal DNA sequence are detected in certain patients or transcriptions for Northern Blot Assay and/or a DNA for In situ hybridization assays may be produced with these latter probes.

The measured ratio of AR to HSRNAAM can be greater or smaller than that required in healthy individuals. The normal value in healthy individuals can be determined in a simple manner, for example by measuring the ratio of AR to HSRNAAM in number of healthy test subjects. By comparison of this normal value with that measured in a patient to be tested it can be established whether or not the value in the patient is greater or less than the normal value.

The concentration of HSRNAAM and/or AR can be different in different tissues. For example the concentration of HSRNAAM in the antechamber of the heart, the marrow, the thymus and uterus is very large, while in contrast the concentration in the liver, lungs and prostate can be comparatively smaller. The different concentrations in the different tissues must be considered during the testing. That means that the test value and the normal or standard value compared should be from the same type of tissue.

Another possibility for determination of defects in the co-modulation mechanism between AR and HSRNAAM can be based on only measuring only the concentration of HSRNAAM, while assuming that the AR concentration is at least approximately constant. If a less than normal HSR-NAAM concentration is measured, that means that the ratio of AR to HSRNAAM has shifted, which suggests interference with the co-modulation mechanism.

It is also possible to determine changes in the HSRNAAM expression and thus in the ratio of it to AR with an HSRNAAM specific probe. These changes can be involved in starting different illnesses or as consequence of them.

This surprising knowledge that, for example, an androgen resistant syndrome can be based on interference or disturbance of the equilibrium between AR and HSRNAAM prevalent in the target cells rests on the finding and characterization of HSRNAAM as co-modulator obtained from the measurements of the AR/HSRNAAM ratios. Too much HSRNAAM can lead to an over-sensitivity of the AR system, so that it reacts to molecules, which normally have no androgenic effect. The reverse leads to the absence or missing function of HSRNAAM to all levels of androgen resistance. The detection of too much HSRNAAM in patients calls for use of means for down-regulation, such as anti-sense or similar medicines, in order to reduce the HSRNAAM titer in certain patients under clinical conditions. This can be achieved by molecules, which are in a position to inhibit the interaction between AR and HSR-NAAM. If a patient has too little HSRNAAM, then HSR-NAAM-cDNA, -protein or -DNA can be administered to him by different known mechanisms to increase the titer of the active HSRNAAM in this way. It is possible also to increase the concentration or the activity of the HSRNAAM by small molecule drugs or by stimulation of the self-synthesis with the aid of specific HSRNAAM promoter proteins.

BRIEF DESCRIPTION OF THE SEVERAL VIEWS OF THE DRAWING

The objects, features and advantages of the invention will now be illustrated in more detail with the aid of the following description of the preferred embodiments, with reference to the accompanying figures in which.

The following examples serve to illustrate the claimed invention without further limiting it.

EXAMPLES

Example 1

A screening by a conventional two hybrid yeast system in the presence of androgen $10^{-6}$ M DHT is performed using a cDNA library from fetal liver (Clontech MATCHMAKER) and a human AR fragment, which codes for the amino acids 325 to 919, as probe. In agreement with the recommendations of the manufacturer (Clontech) the number of screened clones amounted to $2\times10^7$. The number of independent clones amounts to $3.5\times10^6$ according to the public statements of the manufacturer. From those 300 positive clones were selected and tested with a β-galactosidase assay. Of those latter clones 40 were reported as lacZ-positive clones. The inserts of these clones were amplified with PCR. At least 39 different clones were identified by restriction fragment analysis and sequencing. One of those was a clone with an insert comprising 1110 bp (986 bp to 2096 bp), which coded for a part of the ORF (open reading frame) of HSRNAAM (Genbank access number X99209).

The fragment comprising 499 bp (986 bp to 1485 bp) of HSRNAAM-cDNA sequence served as probe for human blot. The tissue distribution of the arginine methyl transferase was determined (FIG. 2) by a Northern Lights Human Multiple mRNA Blot (Life Technologies). A transcript was found using the HSRNAAM probe.

Figure 1:
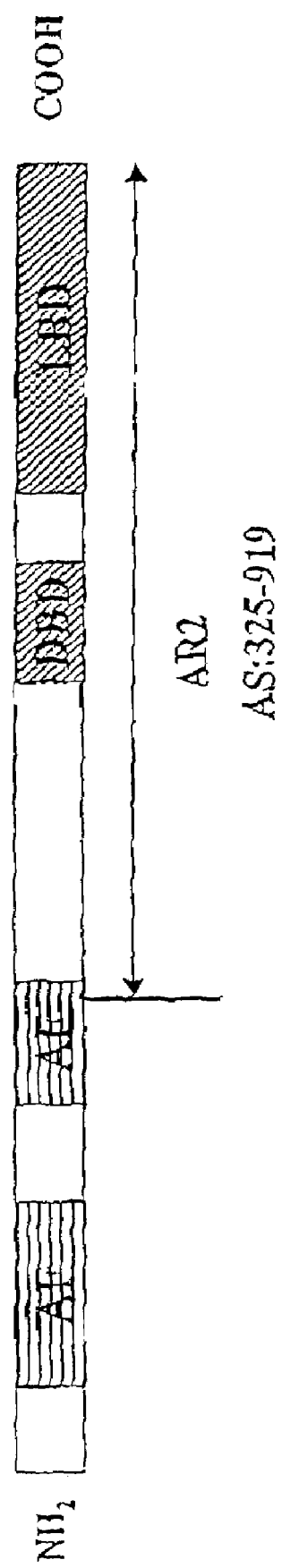
FIG. 1 is a schematic diagram of the androgen receptor showing the androgen receptor domain (AR2) from amino acid 325 to 919, which is able to interact with HSRNAAM in the presence of androgens.
Figure 2:
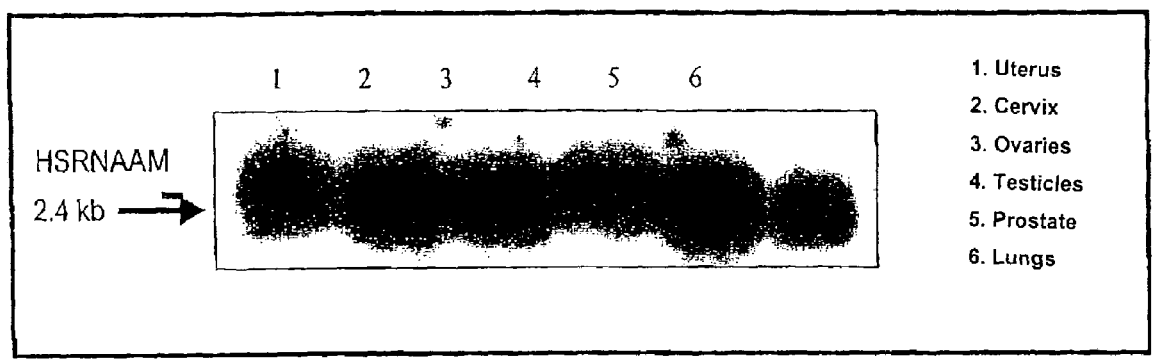
FIG. 2 is an illustration showing the distribution of HSRNAAM in various different human tissues.

FIG. 2 shows the tissue distribution of HSRNAAM, which was tested by a Northern Blot Analysis in a known manner. Poly-$A^+$-RNA isolated from different human tissues, which was normalized to β-aktin, was separated with a formaldehyde-containing agarose gel, blotted on a NYLON® membrane and hybridized with a normalized HSRNAAM-cDNA fragment (986 to 1485 bp). A transcript was found in different human tissues (FIG. 2).

The HSRNAAM-cDNA fragment from 986 bp to 1485 bp (AS 271–433) amplified by the PCR and specific primer from the yeast vector was cloned with the endonucleases EcoRI and Xhol in the usual way in the vector pCMV-NFκB and the HSRNAAM-cDNA fragment from 177 bp to 1485 bp (AS 1–433) amplified by specific primer from human universal cDNA (Clontech) was cloned with the endonucleases EcoRI and Xhol in the usual way in the vector pCMX and with MMTV luciferase in PC3-ARwt cells, which express AR, similarly transfixed.

Figure 3:
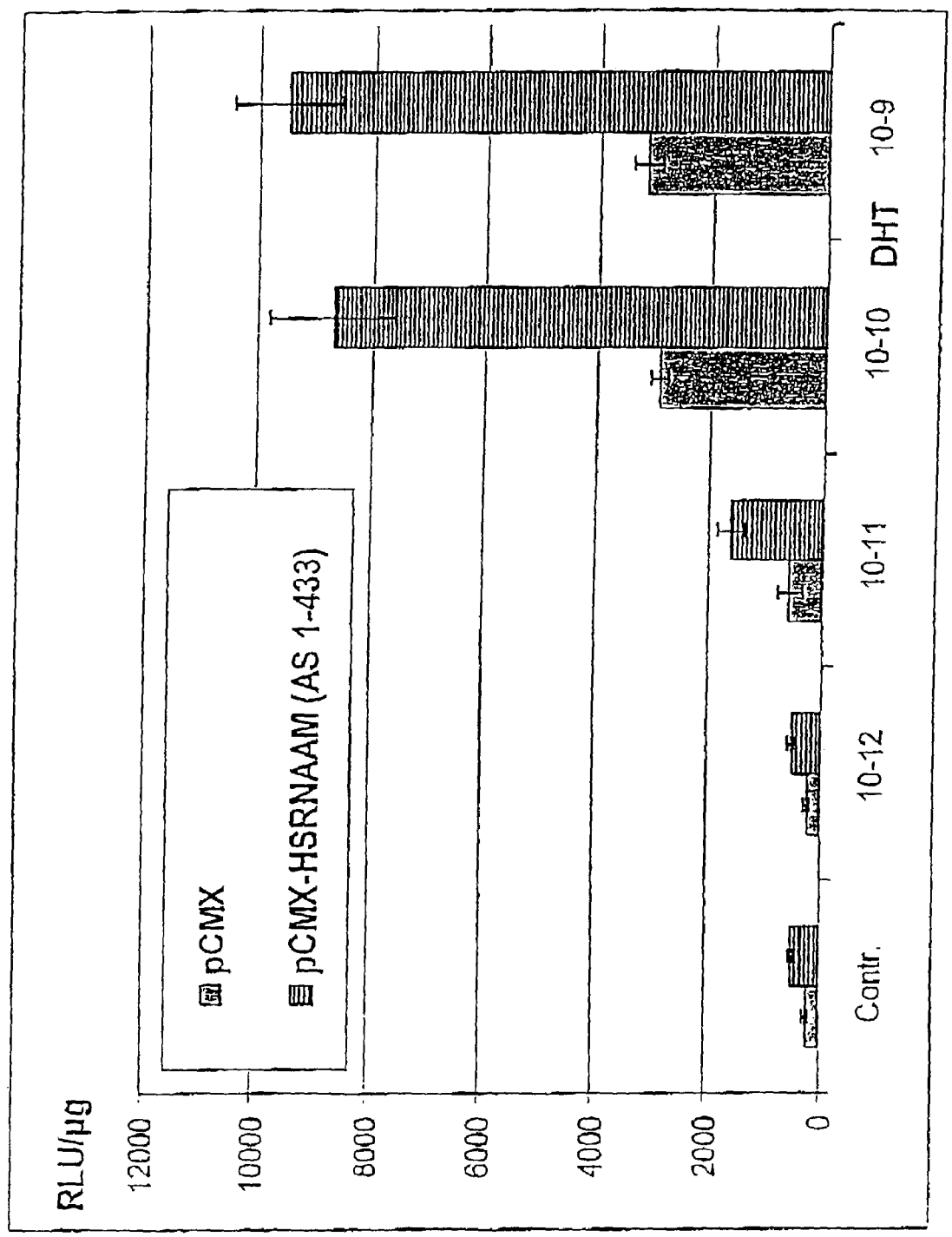
FIG. 3 is a graphical illustration showing the action of HSRNAAM (AS 1–433) as co-modulator with the androgen receptor in PC3-ARwt cells.
Figure 4:
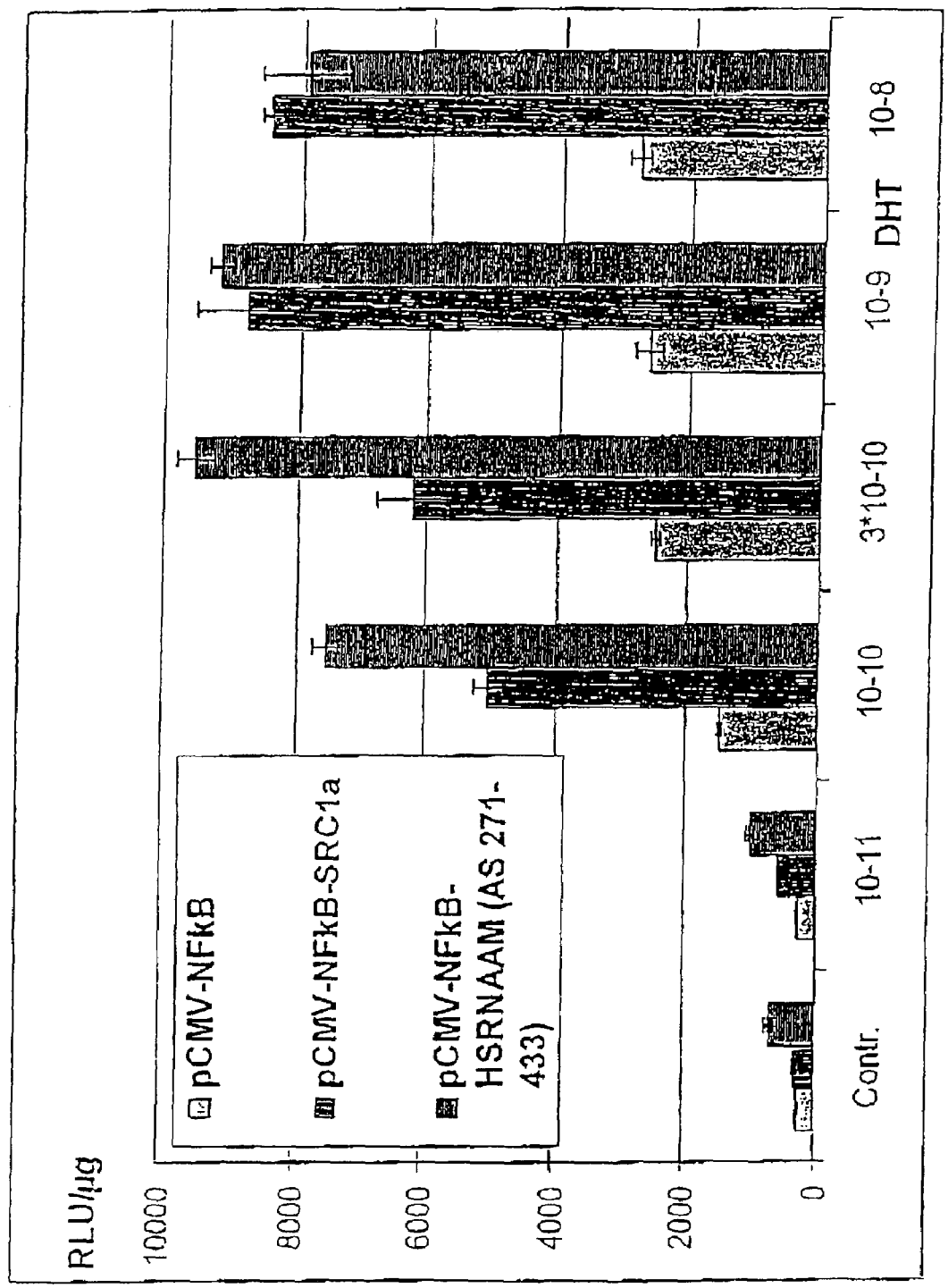
FIG. 4 is a graphical illustration showing the interaction of an HSRNAAM fragment (AS 271–433) or SRC-1a with the androgen receptor in PC3-ARwt cells.

As shown in FIG. 3 the transient transfection of HSR-NAAM-cDNA (AS 1–433) in PC3-Arwt cells leads to a strong co-modulation of the AR signal activity and the arginine methyl transferase acts as co-activator for the nuclear receptor. Further the transient transfection of the HSRBAAM-cDNA fragment (AS 271–433) fused in frame with the transactivated domain from NFκB in PC3-Arwt cells leads to a strong co-activation of the AR signal activity (FIG. 4), which indicates an interaction between the arginine methyl transferase and the nuclear receptor or other co-modulators. Those were transfixed with 1.0 µg MMTV luciferase plasmid and with 0.5 µg of pCMX-HSRNAAM construct (AS 1–433) and/or with 0.35 µg pCMV-NFκB as negative control or with 0.5 μg pCMV-NFκB-SRC1a as positive control in respective cavities having 2×10$^5$ cells per cavity in a cell culture dish. The transfixed cells were treated 24 hours with dihydroxytestosterone (DHT) in the stated concentrations and harvested after another 24 hours, before measuring the activity of the reporter gene (Luciferase). Additionally the entire cell protein amounts were determined for normalization. Two experiments with three measurements each were performed for each transfection initiation and substance concentration. The error variation was reported as SD. The activity is given in relative units.

The disclosure in German Patent Application 102 26 675.1 of Jun. 12, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method for testing for hormonal effects of substances, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of testing for hormonal effects of a substance, said method comprising the steps of:

a) transfecting cells with two vectors, wherein a first of the two vectors contains a DNA, which codes for a nuclear receptor protein or for a fragment of said nuclear receptor protein having an AF-2 domain as well as nuclear receptor properties and functions, and a second of the two vectors contains a DNA coding for an arginine methyl-transferase co-modulator or a DNA coding for a fragment of said arginine methyltransferase co-modulator, wherein said DNA coding for said arginine methyltransferase co-modulator has a nucleotide sequence set forth in SEQ ID NO: 2 and said DNA coding for said fragment of said arginine methyltransferase co-modulator has a nucleotide sequence set forth in SEQ ID NO: 3;

b) exposing said cells transfected with said first of said Two vectors and with said second of said two vectors to said substance; and c) measuring transcription activity indicated by the activity of a reporter gene operably linked to a promoter activated by said nuclear receptor protein or activated by said fragment thereof in the presence of said substance and in the presence of said arginine methyltransferase co-modulator or said fragment of said arginine methyltransferase co-modulator, wherein said hormonal effects are indicated by elevated or reduced transcription activity due to the presence of the substance, measuring an effect or influence of the substance on an interaction of said nuclear receptor protein or said fragment of said nuclear receptor protein with said arginine methyltransferase co-modulator or said fragment of said arginine methyltransferase co-modulator, wherein the hormonal effects of the substance are indicated by a change in said interaction due to the presence of the substance during the measuring, and said change in said interaction is indicated by the activity of reporter gene operably linked to a promoter which Is activated by the interactcion of said nuclear receptor protein or said frament of said nuclear receptor protein with said arginine methyltransferase co-modulator or said fragement of said arginine methyltransferase co-modulator.

2. The method as defined in claim 1, wherein said nuclear receptor protein is selected from the group consisting of androgen receptor, estrogen receptor α, estrogen receptor β, progesterone receptor A, progesterone receptor B, glucocorticoid receptor, mineral corticoid receptor, thyroid gland hormone receptor, vitamin D receptor, peroxisome proliferator-activator receptor, retinoic acid receptor and retinoid X receptor.

3. The method as defined in claim 1, wherein said cells are selected from established cell lines and/or are eukaryotic cells.

4. The method as defined in claim 1, wherein said vectors are eukaryotic expression vectors and said cells are eukaryotic cells selected from the group consisting of prostate cells, nerve cells, glia cells, fibroblast cells, blood cells, osteoblast cells, osteoclast cells, hepatocytes, epithelial cells and muscle cells.

5. The method as defined in claim 1, wherein said hormonal effects are androgenic or anti-androgenic effects.

6. The method as defined in claim 1, wherein said nuclear receptor protein is an androgen receptor protein, said fragment of said nuclear receptor protein is a fragment of said androgen receptor protein, and DNA coding for said androgen receptor protein has a nucleotide sequence set forth in SEQ. ID. NO: 1 and said fragment of said androgen receptor protein has androgen receptor functions and properties equivalent to those of said androgen receptor protein.

7. A method of indicating the presence of an androgen-conditioned malady or disease in a human patient, said method comprising measuring, outside a body of the patient, at least one of a concentration of an arginine methyltransferase co-modulator or of a fragment of said arginine methyltransferase co-modulator, and a concentration of androgen receptor protein or of a fragment of said androgen receptor protein, present in the patient, wherein said arginine methyltransferase co-modulator is coded by a DNA having a nucleotide sequence set forth in SEQ ID NO: 2, said fragment of said arginine methyltransferase co-modulator is coded by a DNA having a nucleotide sequence set forth in SEQ ID NO: 3, said androgen receptor protein is coded by a DNA having a nucleotide sequence set forth in SEQ ID NO: 1 and said fragment of said human androgen receptor protein has an AF-2 domain as well as androgen receptor properties and functions corresponding to those of said human androgen receptor protein;

wherein the presence of the androgen-conditioned malady or disease is indicated or signaled by a change of at least one of said concentration of said arginine methyltransferase co-modulator or of said fragment of said arginine methyltransferase co-modulator and said concentration of said androgen receptor protein or of said fragment of said androgen receptor protein, relative to normal concentration values thereof for said patient.

8. The method as defined in claim 7, wherein said measuring of said at least one of said concentration of said arginine methyltransferase co-modulator or of said fragment thereof and said concentration of said human androgen receptor protein or of said fragment thereof as well as said normal concentration values, takes place by radio-immunoassay, ELISA test, immuno-dyeing or protein chip.

9. The method as defined in claim 7, wherein said androgen-conditioned disease or malady is prostate cancer, erectile dysfunction, infertility, acne, hypogonadism or an androgen-resistance syndrome.

* * * * *